(12) United States Patent
Rubinstein et al.

(10) Patent No.: US 7,189,414 B2
(45) Date of Patent: *Mar. 13, 2007

(54) CONTROLLED RELEASE ORAL DRUG DELIVERY SYSTEM

(75) Inventors: Abraham Rubinstein, Jerusalem (IL); Michael Friedman, Jerusalem (IL); Muhammad Baluom, Taibei (IL); Boaz Tirosh, Holon (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 29 days.

This patent is subject to a terminal disclaimer.

(21) Appl. No.: 10/630,917

(22) Filed: Jul. 31, 2003

(65) Prior Publication Data

US 2004/0219216 A1 Nov. 4, 2004

Related U.S. Application Data

(63) Continuation of application No. 08/750,674, filed as application No. PCT/US95/07519 on Jun. 13, 1995, now Pat. No. 6,692,766.

(30) Foreign Application Priority Data

Jun. 15, 1994 (IL) .................................. 110024

(51) Int. Cl.
*A61K 9/10* (2006.01)
*A61K 9/22* (2006.01)
*A61K 47/32* (2006.01)
*A61K 47/38* (2006.01)

(52) U.S. Cl. ..................... 424/487; 424/488; 424/468; 514/772.6; 514/781

(58) Field of Classification Search ........ 424/484–488, 424/468, 471–472, 450; 514/772.6, 781
See application file for complete search history.

(56) References Cited

U.S. PATENT DOCUMENTS

| 4,568,559 A | | 2/1986 | Nuwayser et al. | |
|---|---|---|---|---|
| 5,160,737 A | * | 11/1992 | Friedman et al. | 424/401 |
| 6,692,766 B1 | * | 2/2004 | Rubinstein et al. | 424/487 |

FOREIGN PATENT DOCUMENTS

EP 252539 A1 12/1987

OTHER PUBLICATIONS

Battaglia, E., et al., Characterization of a New Class of Inhibitors of the Recombinant Human Liver UDP-Glucuronosyltransferase, UGT1*6, Biochimica et Biophysica Acta, 1243 : 9-14 (1995).

Benet, L.Z., et al., "Importance of Drug Metabolism and Antitransport Processes: A Paradigm Shift in Oral Drug Delivery," Proceedings of the 7th International Symposium on Recent Advances in Drug Delivery Systems, Salt Lake City, Utah, pp. 11-14 (1995).

(Continued)

*Primary Examiner*—Edward J. Webman
(74) *Attorney, Agent, or Firm*—Pearl Cohen Zedex Latzer, LLP; Mark S. Cohen

(57) ABSTRACT

The invention relates to synchronous drug delivery composition comprising a polymeric matrix which comprises hydrogel blended with a hydrophobic polymer, so as to form an erodible matrix, a drug, and, optionally, an agent which enhances intestinal drug absorption and/or an agent which inhibits intestinal drug degradation, wherein erosion of the erodible matrix, permits synchronous release of the drug, the hydrogel and the intestinal drug absorption agent and/or the agent which inhibits intestinal drug degradation.

16 Claims, 6 Drawing Sheets

OTHER PUBLICATIONS

Borchard, G., et al., "Multifunctional Polymers for Improved Peroral Peptide Drug Absorption," Proceedings of the 7th International Symposium on Recent Advances in Drug Delivery Systems, Salt Lake City, Utah, pp. 7-10, Bai J. P-F., et al. ibit., pp. 153-154 (1995).

Chao, Y.W. and Flynn, M., "Oral Delivery of Insulin," Lancet, 23 : 1518-1519 (1989).

Damge, C., et al., "New Approach for Oral Administration of Insulin with Polyalkylcyanoacrylate Nanocapsules as Drug Carrier," Diabetes, 37 : 246-251 (1988).

Danforth, Jr., E. and Moore, R.O., "Intestinal Absorption of Insulin in the Rat," Endocrinology, 65 : 118-123 (1959).

Dapergolas, G. and Gregoriadis, "Hypoglyaemic Effect of Liposome-Entrapped Insulin Administered Intragastrically into Rats," Lancet, 2 : 824-827 (1976).

Eudragit® RL Data Sheet (Info RL-3/e). No date given.

Eudragit® RL/RS Standards Sheet (Info RL/RS-7/e). No date given.

Eudragit® RL/RS Technical Application Pamphlet (Info RL/RS-11/e). No date given.

Eudragit® RL/RS Technical Application Pamphlet (Info RL/RS-12/e). No date given.

Eudragit® RL and RS Application in the Production of Pharmaceutical Preparations Prospectus (Info RL/RS-1/e). No date given.

Fahr, A., "Cyclosporin Clinical Pharmacokinetics," Clin. Pharmacokinet., 24(6) : 472-495 (1993).

Geary, R.S. and Schlameus, H.W., "Vancomycin and Insulin Used as Models for Oral Delivery of Peptides," J. Controlled Release, 23 : 65-74 (1993).

Goriya, Y., et al., "Blood Glucose Control and Insulin Clearance in Unrestrained Diabetic Dogs Portally Infused with a Portable Insulin Delivery System," Diabetologia, 19 : 452-457 (1980).

Hochman, J.H., et al., "In vitro and In Vivo Analysis of the Mechanism of Absorption Enhancement by Palmitoylcarnitine," J. Parm. and Exp. Therap., 269 (2) : 813-822 (1994).

Hochman, J. and Artursson, P., "Mechanisms of Absorption Enhancement and Tight Junction Regulation," J. Controlled Release, 29 : 256-267 (1994).

Honesch, H., et al., "Cytochrome P-450 and Drug Metabolism in Intestinal Villous and Crypt Cells of Rats: Effect of Dietary Iron," Biochem and Biophys. Res. Comm., 65(1) : 399-406 (1975).

Kidron, M., et al., "The Absorption of Insulin From Various Regions of the Rat Intestine," Life Science, 31 (25) : 2837-2841 (1982).

Kraeling, M.E.K. and Ritschel, W.A., "Development of a Colonic Release Capsule Dosage Form and the Absorption of Insulin," Meth Find Exp. Clin. Pharmacol., 14(3) : 199-209 (1992).

Lee, V.H.L., et al., "Oral Route of Peptide and Protein Drug Delivery," V.H.L. Lee (Ed.) : Peptide and Protein Drug Delivery, Marcel Dkker, 1991 New York, pp. 691-738.

Morishita, M., et al., "Novel Oral Microspheres of Insulin With Protease Inhibitor Protecting From Enzymatic Degradation," Intl. J. Pharmaceutics, 78 : 1-7 (1992).

Muranishi, S., "Absorption Enhancers," Critical Reviews in Therapeutic Drug Carrier Systems, 7(1) : 1-34 (1990).

Osborne, R., et al., "Morphine and Metabolite Behavior After Different Routes of Morphine Administration: Demonstration of the Importance of the Active Metabolite Morphine-6-Glucuronide," Clin. Pharmacol, Ther., 47(1) : 12-19 (1990).

Patel, H.M. and Ryman, B.E., "Oral Administration of Insulin by Encapsulation Within Liposomes," FEBS Letters, 26(1) : 60-63 (1976).

Peters, W.H.M., et al., "Glutathione S-Transferase, Cytochrome P450, and Uridine 5'—Diphosphate-Glucuronosyltransferase in Human Small Intestine and Liver," Gastroenterology, 96 : 783-789 (1989).

Saffran, M., et al., "A New Approach to the Oral Administration of Insulin and other Peptide Drugs," Science, 233 : 1081-1084 (1986).

Sanders, L.M., et al., "Prolonged Controlled-Release of Nafarelin, A Luteinizing Hormone-Releasing Hormone Analogue, From Biodegradable Polymeric Implants: Influence of Composition and Molecular Weight of Polymer," J. Pharm. Sci., 75(4) : 356-360 (1986).

Sanders, L.M., et al., "Controlled Delivery of an LHRH Analogue From Bjodegradable Injectable Microspheres," J. Controlled Release, 2 : 187-195 (1985).

Schulte-Hermann, R. and Parzefall, W., "Adaptive Responses of Ra Liver to the Gestagen and Anti-Androgen Cyproterone Acetate and other Inducers. I. Induction of Drug-Metabolizing Enzymes," Chem Biol. Interactions, 31 : 279-286 (1980).

Takahashi, K., et al., "Decanoic Acid Induced Enhancement of Rectal Absorption of Hydrophilic Compounds in Rats," Pharmaceutical Res., 11(10) : 1401-1404 (1994).

Takahashi, K., et al., "Pharmacokinetics Analysis of the Absorption Enhancing Action of Decanoic Acid and its Derivatives in Rats," Pharm. Res., 11(3) : 388-392 (1994).

Touitou, E. and Rubinstein, A., "Targeted Enteral Delivery of Insulin to Rate," Intl. J. Pharm., 30 : 95-99 (1986).

Van Hoogdalem, E.J., et al., "Intestinal Drug Absorption Enhancement: an Overview," Pharmac, Ther., 44 : 407-443 (1989).

Wahlström, A., et al., "Tricyclic Antidepressants Inhibit Opioid.. Receptor Binding in Human Brain and Hepatic Morphine Glucuronidation," Phar. & Toxic., 75 : 23-27 (1994).

Weingarten, C., et al., "Oral Ingestion of Insulin Liposomes: Effects on the Administration Route," Life Science, 28 : 2747-2752 (1981).

Ziv, W., et al., Absorption of Protein via the Intestinal Wall, Bochem. Pharmcol, 36(7) : 1035-1039 (1987).

Database WPI, Week 9530, Derwent Publications Ltd., London, GB; AN 95-228636 & JP, A, 07 138 182 (Toyobo et al.), May 30, 1995 Abstract.

\* cited by examiner

CONTROLLED RELEASE ORAL DRUG DELIVERY SYSTEM

CROSS-REFERENCE

This Application is a Continuation Application of U.S. Ser. No. 08/750,674, Jun. 13, 1995 now U.S. Pat. No. 6,692,766 which is the National Phase Application of PCT/US95/07159, filed Jun. 13, 1995, which claims priority from Israel Patent Application No. 110024, filed Jun. 15, 1994, which are incorporated herein by reference.

FIELD OF THE INVENTION

The invention relates to a pharmaceutical system aimed at increasing the bioavailability of orally administered drugs belonging to the following categories: (a) large molecular weight drugs, (b) drugs that lose their potency in the gastrointestinal (GI) tract as a result of enzymatic degradation.

BACKGROUND OF THE INVENTION

In the following paragraphs protein drugs will be discussed as typical examples of drug molecules that are either large molecules or highly susceptible to enzyme degradation. However, additional non-proteinous drugs can be included in this group and they will be discussed later.

Medical use of protein drugs is constrained by three major drawbacks. The first is their short biological half-life which requires, in some cases, frequent administrations. The second is the rapid degradation which occurs in mucosal tissues that generally cover the body cavities. Lastly, most protein drugs are large molecules and therefore do not easily cross the intestinal epithelium. Therefore, the most common mode of protein drugs administration is the parenteral route. However, apart from the inconvenience to the patients, parenteral delivery systems are also more expensive in terms of production and drug administration. There is therefore a need for an effective non-parenteral mode of administration of protein drugs that will provide protection against biological degradation and/or enhance its transport across mucosal barriers. Although sophisticated non-parenteral pharmaceutical systems, such as intra-nasal systems, have been developed, oral administration is more favorable, having the major advantage of convenience for increased patient compliance. Sometimes oral administration of peptides offers physiological advantages, for example oral administration of insulin is superior to parenteral administration because, like the native hormone secreted by the pancreas, it also drains primarily into the portal vein to exert its initial effect on the liver. Some insulin will then find its way into the peripheral circulation via lymphatic channels [Goriya, Y., et al., Diabetologia 19:454–457 (1980)]. In contrast, injected insulin is drained entirely into the peripheral circulation and has access to all parts of the body. Notwithstanding these advantages, most protein drugs have not been orally delivered to date because of the lack of a simple and reliable drug delivery system that will be able to overcome the biological and physico-chemical constraints mentioned above.

An effective oral carrier for protein drugs should (a) shield its content against the luminal and brush border peptidases and (b) be capable of facilitating the uptake of the protein drug—usually a large molecular weight entity—across the gastrointestinal (GI) epithelium. Many studies have reported that protein drugs such as insulin, vasopressin, calcitonin, enkaphalins and thyrotropin-releasing hormone (TRH) were administered relatively successfully via the oral route [Lee, V. H. L., et al., Oral Route of Peptide and Protein Drug Delivery, in V. H. L. Lee (Ed.): Peptide and Protein Drug Delivery, Marcel Dekker, 1991 New York, pp 691–738]. An increase in the bioavailability of protein drugs after oral administration can be accomplished by the co-administration of either peptidases inhibitors, to help keep the protein drug as intact as possible at the site of absorption, or of protein absorption enhancers. Some works report the use of both absorption enhancers and peptidase inhibitors in the same formulation [e.g. Ziv, E., et al., Biochem. Pharmcol. 36:1035–1039 (1987)]. Some typical examples of oral administration of the protein drug insulin together with peptidase inhibitors or absorption enhancers are listed below.

Morishita et al. [Int. J. Pharm. 78:1–7 (1992)] found that after formulating insulin together with protease inhibitors such as trypsin inhibitor, chemostatin, Bowman-Birk inhibitor and aprotinin into Eudragit L-100$^R$ microspheres, the insulin was resistant to pepsin, trypsin and α-chymotrypsin in vitro. However, in similar experiments performed in vivo by Laskowski and coworkers in which insulin was injected together with soybean trypsin inhibitor (SBTI) or, alternatively, without any inhibitor, a very small pharmacodynamic response was observed [Laskowski, M., Jr., et al., Science 127:1115–1116 (1958)]. Similar results were observed by Danforth and coworkers who also found that diisopropylfluorophosphate was an effective depressant of insulin digestion, while SBTI was not [Danforth, E., et al., Endocrinology 65:118–123 (1959)]. In contrast, it was found that the addition of SBTI solution boosted the pharmacological effect of insulin, namely reduction of blood glucose level, after its injection into the lumen of rat ileum [Kidron, M., et al., Life Sci. 31:2837–2841 (1982)]. Takahashi et al. used decanoic acid to enhance the absorption of the hydrophilic non-absorbable marker phenol sulfon phthalate. They found that the absorption correlated to the rate of disappearance of the decanoic acid from the intestine. The absorption onset was within few minutes. This indicates that there is a rationale to apply an absorption enhancer for improved functioning of the delivery system.

Table A and Table B hereunder itemize some examples of absorption enhancers and protease inhibitors reported in the literature.

TABLE A

Classes of enhancers tested to promote drug absorption in the GI tract and some of their representatives
(References listed after Table A)

| CLASS | EXAMPLES |
|---|---|
| NSAID (non-steroidal antiinflammatory drugs) and derivatives | Sodium salicylate<br>Sodium 5-methoxysalicylate<br>Indomethacin<br>Diclofenac |
| Surfactants | Nonionic: polyoxyethylene ethers<br>Anionic: sodium laurylsulfate<br>Cationic: quaternary ammonium compounds |
| Bile salts | Dihydroxy bile salts: Na deoxycholate<br>Trihydroxy bile salts: Na cholate |
| Medium-chain fatty acids | Octanoic acid<br>Decanoic acid |
| Medium-chain glycerides | glyceryl-1-monooctanoate<br>glyceryl-1-monodecanoate |

TABLE A-continued

Classes of enhancers tested to promote drug absorption in the GI
tract and some of their representatives
(References listed after Table A)

| CLASS | EXAMPLES |
| --- | --- |
| Enamines | DL-phenylalanine ethylacetoacetate enamine |
| Mixed micelles | Glyceryl monooleate + Sodium taurocholate Linoleic acid + HCO60 |
| Calcium binding agents | EDTA |
| Phenothiazines | Chlorpromazine |
| Liposomes | |
| Azone | |
| Fatty acid derivatives of carnitine and peptides | Palmitoyl-DL-carnitine N-myristoyl-L-propyl-L-prolyl-glycinate |
| Saponins | Concanavaline A |
| Phosphate and phosphonate derivatives | DL-$\alpha$-Glycerophosphate 3-Amino-1-hydroxypropylidene-1,1-diphosphonate |
| Polyacrylic acid | |
| Decanoic acid | |

REFERENCES van Hoogdalem E. J. et al., Pharmac. Ther. 44:407–443 (1989);

Muranisbi S., Crit. Rev. Ther. Drug Carrier Sys., 7:1–34 (1990);

Geary, R. S. and Schlemeus, H. W., J. Contr. Release, 23:65–74 (1993);

Touitou, E. and Rubinstein A., Int. J. Pharm. 30:95–99 (1986);

Kraeling, M. E. K. and Ritschel, W. A., Meth. Find. Exp. Clin. Pharmacol. 14:199–209 (1992)].

Takahashi, K. et al., Pharm. Res. 11:388–392 (1994);

Takahashi, K. et al., Pharm. Res. 11:1401–1404 (1994);

Hochman, J. H. et al., J. Pharmacol. Ex. Ther. 269:813–822 (1994).

TABLE B

Examples of protease inhibitors used in oral formulations
of peptide drugs

| SUBSTRATE | REFERENCE |
| --- | --- |
| Aprotinin | Kidron et al. Life Sci. 31: 2837 (1982); Morishita, M. et al., Int. J. Pharm. 78: 1–7 (1992) |
| SBTI | Laskowski et al. (1958) ibid; Danforth et al. (1958) ibid; Kidron et al. (1982) ibid; Bowman-Birk inhibitor Morishita et al. (2) (1992) ibid. |
| Polycarbophil | Borchard G. et al., Proceedings of the 7th International Symposium on Recent Advances in Drug Delivery Systems, Salt Lake City, Utah, February–March, 1995, pp. 7–10. |
| Bowman-Birk inhibitor | Morishita et al., Int. J. Pharm. 78: 1–7 (1992) |

Absorption enhancement has been found to be very efficient in the improvement of the bioavailability of poorly soluble drugs especially in organs such as the nasal cavity and the rectum where prolongation of the drug delivery system's residence time can be accomplished relatively easily [Hochman J. and Artursson P., J. Contr. Rel., 29:253–267 (1994)]. However, data on the enhancement of drug uptake in the GI tract are available primarily from in vitro studies. In such kind of studies the absorption modulator(s) is placed (or perfused in a constant rate) over unreal period of time. Some studies reported on prolonged pharmacological effect [Geary R. S. and Schlameus H. S., J. Contr. Release 23:65–74 (1976); Damge', et al., Diabetes 37:246–251 (1988)]. This effect was achieved either when relatively high amounts of absorption enhancers were used, or when microparticles and bioadhesion techniques were employed. Under normal conditions the motility of the small intestine pushes a solid dosage form so that it stays very briefly in the vicinity of the absorbing mucosa. Therefore it is reasonable to assume that a controlled release technology is required to "seed" constant amounts of enhancer(s) along the digestive tube. Yet, the absorption modulator should be released in a rate similar to the release rate of the protein drug. The simplest way to achieve such a synchronization would be with a large, erodible dosage form. It will be difficult for a particulate dosage form to accomplish such synchronization because the spreading effect caused by gastric emptying under fasted conditions. Table C hereunder summarizes some techniques for the oral delivery of peptide drugs based on ordinary controlled release concepts.

When a protein drug is formulated together with an absorption enhancer and/or peptidase inhibitor into an oral dosage form, the rate of supply of the formulation functional ingredients into the aqueous mildew of the GI tract becomes crucial. It is important for the release rates to be slow and controllable [i.e. the release rates of the protein drug, the peptidase inhibitor(s) and/or the absorption enhancer(s) must all be slow and synchronized] for the following reasons: (a) To improve its absorption the protein drug should be continuously accompanied by its "guard" molecules, i.e. the peptidase inhibitor or the absorption enhancer, or both of them, until the drug's absorption has been completed; (b) A synchronzed slow release from the delivery system will ascertain a prolonged drug supply to the body which will result in a desired and sufficient pharmacodynamic response, hereby overcoming the limitation of the short biological half life of the protein drug; (c) An uncontrollable, immediate release of the protein drug together with the protease inhibitor and/or the absorption enhancer (from dosage forms such as enteric coated capsules, or microcapsules or microparticulate delivery systems) could cause an unrestrained dilution of the drug with the fluids of the alimentary canal. This might reduce the concentration of the drug into values below those required to maintain effective concentration gradients across the intestinal epithelium; (d) Since various formulation components (the protein drug, the absorption enhancer and the protease inhibitor) differ from each other by their physico-chemical properties (solubility, dissolution constants, mode of dissolution, and partition coefficients) difficulties are likely to arise in the design of an oral delivery system of protein drugs, especially the systems that release their drug content in a burst manner (enteric coated capsules), or rely on diffusion throughout a membrane (microcapsules, coated tablets).

TABLE C

Examples for controlled release techniques for oral delivery of protein drugs relying on non-synchronized drug diffusion from capsules, microcapsules, microemulsions or erodible polymers

| TECHNIQUE | REFERENCE |
|---|---|
| Colonic delivery using insulin-containing soft gelatin capsules coated with mixtures of various ratios of polyacrylic polymers having different pH-dependent solubility properties (Eudragit$^R$ RS, L and S) | Touitou, E. and Rubinstein A., Int. J. Pharm. 30: 95–99 (1986) |
| Entrapment of insulin in liposomes that presumable provide mechanical protection against proteolysis | Weingarten, C., et al., Life Sci. 28: 2747–2751 (1981); Dapergolas G., Gregoriadis G., Lancet 2: 824–827 (1976); Patel H. M., Ryman B. E., FEBS Lett. 62: 60–63 (1976) |
| Microemulsions (insulin and aprotinin in the aqueous phase, and lecithin, non-esterified fatty acids, and cholesterol in the oily phase). For convenience of administration, the microemulsion was sprayed onto an inert carrier (calcium carboxymethylcellulose), and placed in hard gelatin capsules | Cho, Y. W. and. Flynn, M., Lancet 2: 1518–1519 (1989) |
| Colonic delivery using mixtures of insulin microemulsions Cab-O-Sil$^R$ filled gelatin capsules pretreated with formaldehyde vapor and coated with Eudragit NE 30D, Eudragit S100, and finally with cellulose acetate phthalate coat | Kraeling M. E. K. and Ritschel W. A. Meth. Find. Exp. Clin Pharmacol. 14: 199–209 (1992) |
| Insulin-containing nanocapsules made of polyalkylcyanoacrylate | Damge' C., et al. Diabetes 37: 246–251 (1988) |
| Insulin and protease inhibitor microspheres that were incorporated into an enteric-coating (with Eudragit L-100) carrier | Morishita, M., et al., Int. J. Pharm. 78: 1–7 (1992) |
| Colonic delivery of insulin (and also lysinevasopressin) using coats of copolymers of styrene and hydroxyethylmethacrylate cross-linked with azoaromatic groups | Saffran, M., et al., Science 233: 1081–1084 (1986) |
| Micro matrices of poly(d,l-lactide) or PLGA for the sustained release of LHRH analogue or interferon | Sanders L. M. et al., J. Pharm. Sci., 73: 1294, 1984; Sanders L. M. et al., J. Contr. Rel. 2: 187, 1985 |

There are some non-proteinous drugs that suffer from similar constraints upon oral administration. It is well recognized now& that the Phase I metabolic enzyme cytochrome P-450 is active in the intestinal brush border. In the rat the villus tip cells contain higher amounts of this enzyme than the crypt cells, and the enzyme content in the small intestine is larger than the colon [Hoensch H. et al., Biochem. Biophys. Res. Commun. 65:399–406 (1975)]. A longitudinal gradient of Cyto-chrome P-450 exists also in humans [Peters W. H. M. et al., Gastro-enterology, 93:783–789 (1989)]. As a result, drugs such as benzphetamin [Oshinski R. J. and Strobel H. W., Int. J. Biochem. 19:575–588 (1987)] and cyclosporine [Benet L. Z., et al., Proceedings of the 7th International Symposium on Recent Advances in Drug Delivery Systems, Salt Lake City, Utah, pp. 11–14 (1995)] are susceptible to first-pass brush border metabolism and their bioavailability is decreased significantly. Appropriate cytochrome P-450 inhibitors such as metyrapone, n-octylamine or propafenone, if formulated in erodible delivery systems as described above, may be able to provide reasonable protection to such drugs after oral ingestion. It is noteworthy that although being an oligopeptide, cyclosporine is not metabolized by the gut peptidases but rather by cytochrome P-450-dependent monooxygenase [Fahr A., Clin. Pharmacokin. 24:472–495 (1993)].

An example for a drug that undergoes brush border metabolism after oral administration and could benefit from being incorporated into an erodible delivery system with suitable enzyme inhibitor is morphine which is degraded by mucosal glucuronyl transferase. Its bioavailability after oral administration is much lower than after parenteral administration [Osborne R. et al., Clin. Pharmacol. Ther. 47:12–19 (1990)].

TABLE D

Examples of drugs that undergo enzymatic degradation in the intestinal mucosa [Johann W. Faigle, in Colonic Drug Absorption and Metabolism, Peter R. Bieck ed. Marcel Dekker, Inc. New York.Basel.Hong Kong, p.40 (1993)]

| SUBSTRATE | ENZYME |
|---|---|
| Chlopromazine | Cytochrome P-450 |
| Ethinylestradiol | Cytochrome P-450, sulfotransferase |
| Flurazepam | Cytochrome P-450 |
| Morphine | Glucuronyl tranferase |
| Lorazepam | Glucuronyl tranferase |

A rational design for an oral delivery system of a protein drug would therefore be one in which the synchronized release is accomplished by an erodible matrix. In such a dosage form the release of the protein drug and the functional adjuvants do not depend upon intrinsic diffusion processes but rather are the result of the rate of the matrix erosion. By stripping off the erodible matrix layers in a well controlled manner predetermined amounts of the drug and its "guards", the protease inhibitor(s) and the absorption enhancer(s), will be placed together along the desired segment of the GI tract so that constant and optimal drug blood concentrations are achieved. The successful functioning of the matrix tablets depends upon the ability to "fine tune" its erosion rate. Superior performance can be achieved if part of the matrix tablet components are able, by virtue of their own properties, to serve as peptidase inhibitors. Typical examples of these kinds of polymers are the loosely crosslinked acrylic polymers Carbopol and polycarbophil (PCP). It has been shown that they provide protection to some peptide drugs [Borchard G. et al. Proceedings of the 7th International Symposium on Recent Advances in Drug Delivery Systems, Salt Lake City, Utah, 1995, pp. 7–10,Bai J. P-F., et al., ibid., pp. 153–154]. A major drawback of these polymers for the purpose of the suggested technology is their extremely high swelling properties which cause them to disperse in aqueous solutions within 30 minutes. Therefore a supportive, hydrophobic polymer such Eudragit$^R$ RL must be incorporated into the matrix delivery system (e.g. by forming a polymer blend) in order to achieve a firm hydrogel which will erode (but not create a diffusional barrier) and to establish a control over the erosion rate of the dosage form.

Hydrogel forming materials such as the above mentioned polycarbophil or the polycarbophil blend with Eudragit$^R$ RL must be able to swell in the GI tract and at the same time erode. If they only swell, they will create a diffusional barrier (a conventional sustained release formulation) that will risk the synchronized release. For the purpose of erodible matrix hydrogels additional materials can be used. Some good candidates for this are saccharidic hydrogels such as natural gums and their salts, e.g. alginic acid and its calcium salt—calcium alginate, or pectin and its calcium salt calcium pectinate. If formulated properly these polysaccharides form hydrogels that exchange ions with the GI physiological fluids. As a result they lose their mechanical strength and erode while swelling in a controllable manner.

SUMMARY OF THE INVENTION

The present invention relates to a controlled release drug delivery system comprising a drug which is susceptible to enzymatic degradation by enzymes present in the intestinal tract; and a polymeric matrix which undergoes erosion in the gastrointestinal tract comprising a hydrogel-forming polymer selected from the group consisting of (a) polymers which are themselves capable of enhancing absorption of said drug across the intestinal mucosal tissues and of inhibiting degradation of said drug by intestinal enzymes; and (b) polymers which are not themselves capable of enhancing absorption of said drug across the intestinal mucosal tissues and of inhibiting degradation of said drug by intestinal enzymes; wherein when the matrix comprises a polymer belonging to group (b) the delivery system further comprises an agent which enhances absorption of said drug across the intestinal mucosal tissues and/or an agent which inhibits degaradation of said drug by intestinal enzymes and when the matrix comprises a polymer belonging to group (a) the delivery system optionally further comprises an agent which enhances absorption of said drug across the intestinal mucosal tissues and/or an agent which inhibits degaradation of said drug by intestinal enzymes.

The drug delivery system of the invention further provides a method for orally administering a drug which is susceptible to degradation by enzymes present in the intestine, or mixture of such drugs, to a patient in need of such drug.

The delivery system of the invention provides for the controlled release of not only the drug, but also of the inhibitor of the drug-degrading enzyme and/or the drug absorption enhancer. This synchronized release of the enzyme inhibitor and/or the absorption enhancer furnishes a constant protection against enzymatic degradation of the drug, which is also released from the hydrogel formed by contact with the physiological fluids in a sustained manner, upon the erosion thereof.

The invention also relates to a method of preparing the pharmaceutical delivery system according to the invention.

B: Mean blood insulin levels after oral administration of lactose tablets containing (a) 600 I.U. of insulin, (b) 40 mg of soy bean trypsin (SBTI) inhibitor and (c) 100 mg of sodium cholate to three pancreatectomized dogs. Shown are the mean values±S.D.

DETAILED DESCRIPTION OF THE INVENTION

It is suggested that the in vivo formation of an erodible hydrogel, which contains a drug which may be susceptible to enzymatic degradation, an inhibitor of the enzyme/s which may degrade said drug and an agent which enhances the absorption of said drug across intestinal mucosa, in the presence of physiological fluids of the gastrointestinal (GI) tract, particularly in the intestine, upon oral administration, causes a simultaneous release of the entrapped drug, the enzyme inhibitor and the absorption enhancer. This, in turn, would inhibit the enzymatic degradation of the drug and facilitate its absorption. Therefore, matrix dosage forms incorporating a suitable hydrogel-forming polymer, a drug which is susceptible to enzymatic degradation or a high molecular weight drug (such as protein drug), an enzyme inhibitor (such as protease inhibitor) and an absorption enhancer may serve as a platform for sustained oral delivery system of such drugs.

Figure 1A:
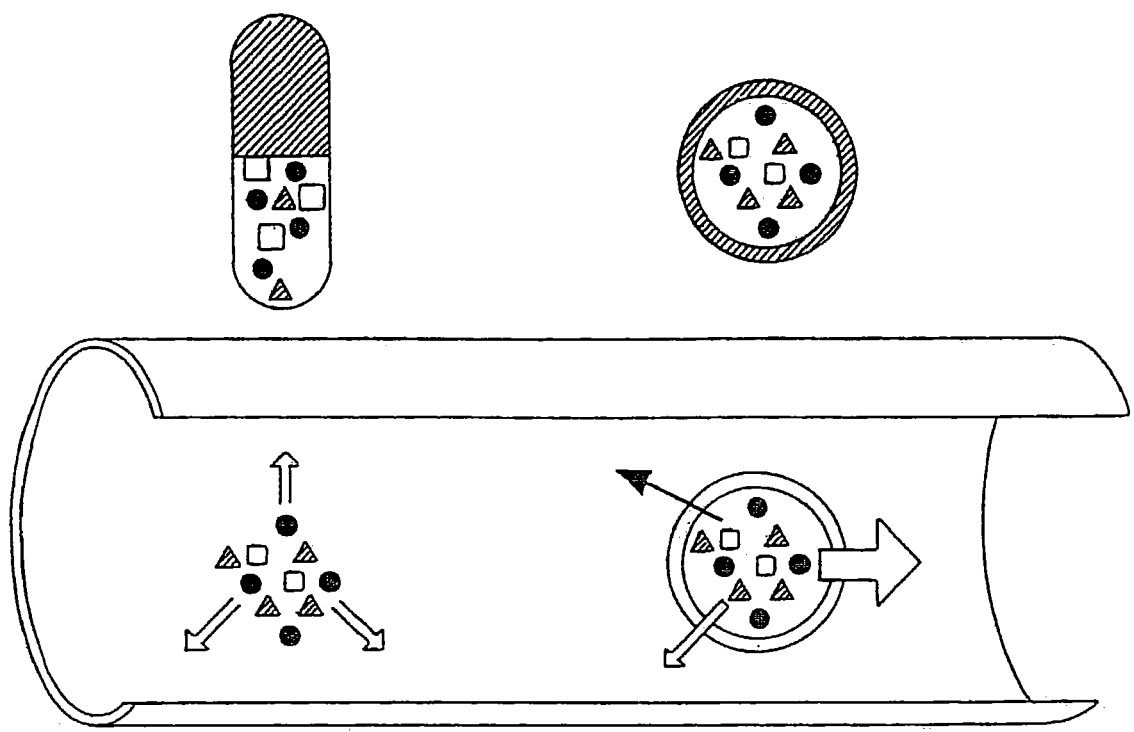
FIG. 1: Pictorial scheme of the erodible hydrogel solid platform concept for the oral delivery of large molecular weight drugs or drugs susceptible to enzymatic degradation in the GI tract.
Figure 1B:
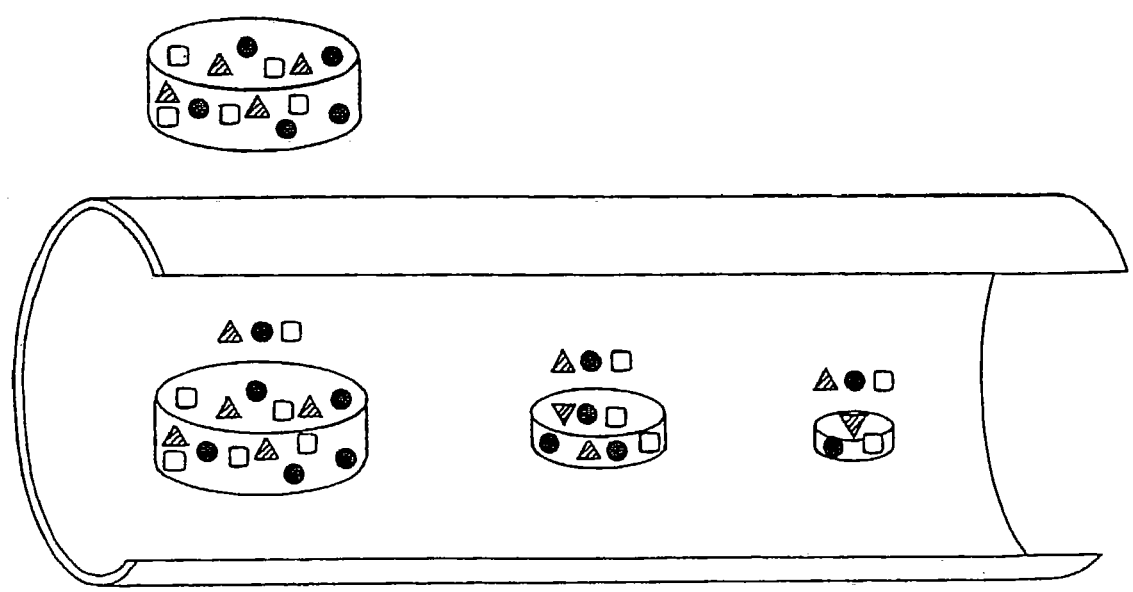

The drug delivery system of the invention is schematically illustrated in FIG. 1 which is a pictorial scheme of the erodible hydrogel solid platform concept for the oral delivery of large molecular weight drugs or drugs susceptible to enzymatic degradation in the GI tract. FIG. 1A shows a non-synchronized delivery system, which can be in either of the following dosage forms: (a) A capsule which dissolves rapidly and releases its contents immediately. As a result the drug (D), the enzyme inhibitor (PI) and the absorption enhancer (AE) are diluted in the intestinal contents, dissolve in individual rates and cannot supply protection or supportive absorption enhancement to the drug. (b) A coated tablet or microcapsules, in which the protective coat creates a diffusional barrier. In this case each one of the dosage form components will leach out of the dosage form at a different rate causing the drug to remain without its functional adjuvants in the intestinal milieu. (c) An erodible hydrogel which erodes while moving along the digestive tube resulting in a synchronized release of the drug, the enzyme inhibitor and the absorption enhancer. The simultaneous release depends on the erosion rate of the carrier and not on the physico-chemical properties of the ingredients. In this technology the enzyme inhibitor or the absorption enhancer could be the hydrogel itself. The erosion dependent rate of the components release will result in a similar effect as described in FIG. 1B.

Thus, the present invention relates to a controlled release drug delivery system comprising a drug which is susceptible to enzymatic degradation by enzymes present in the intestinal tract; and a polymeric matrix which undergoes erosion in the gastrointestinal tract comprising a hydrogel-forming polymer selected from the group consisting of (a) polymers which are themselves capable of enhancing absorption of said drug across the intestinal mucosal tissues and of inhibiting degradation of said drug by intestinal enzymes; and (b) polymers which are not themselves capable of enhancing absorption of said drug across the intestinal mucosal tissues and of inhibiting degradation of said drug by intestinal enzymes; wherein when the matrix comprises a polymer belonging to group (b) the delivery system further comprises an agent which enhances absorption of said drug across the intestinal mucosal tissues and/or an agent which inhibits degradation of said drug by intestinal enzymes and when the matrix comprises a polymer belonging to group (a) the delivery system optionally further comprises an agent which enhances absorption of said drug across the intestinal mucosal tissues and/or an agent which inhibits degradation of said drug by intestinal enzymes.

The major utility of the delivery system according to the invention is for the oral delivery of peptide drugs. However, it also can be used for the delivery of non-proteinous, poorly absorbed drugs or drugs that are susceptible to brush border metabolism.

In one aspect, the invention relates to a controlled release oral drug delivery system comprising a drug which is susceptible to enzymatic degradation in the intestine and a polymeric matrix comprising a hydrogel-forming polymer which by virtue of its own properties can serve as an absorption enhancer or enzyme inhibitor or both, namely polymers belonging to the said group (a).

Examples of said group (a) polymers are hydrogel-forming polymers which exhibit properties of enzyme inhibition and enhancement of drug absorption acrylic acid, acrylic acid derivatives or combinations thereof. Preferred such polymers are acrylic acid derivatives such as polycarbophil or Carbopol.

In a second aspect of the invention, and of the same concept, is controlled release drug delivery system in which the matrix comprises a polymer selected from said group (b). In embodiments according to this aspect of the invention the polymeric matrix comprises, apart from the polymer and drug entrapped therein, at least one agent which is capable of inhibiting enzymatic degradation of the drug in the intestine and at least one agent which enhances the absorption of the drug across intestinal mucosal tissues.

The group (b) hydrogel-forming polymer may be cellulose derivatives, for example, methylcellulose, carboxymethyl cellulose or hydroxypropyl cellulose, acrylic acid or acrylic acid derivatives, for example methylmethacrylate, or a combination thereof. The hydrogel-forming polymer may be a blend of polymers (for example, a blend of polycarbophil and Eudragit$^R$ RL-100). Alternatively, the hydrogel-forming polymer may be a natural polymer, for example guar gum, acacia gum, agar, tragacanth, alginic acid, dextran, arabinogalactan, pectin, egg albumin, soybean protein or hyaluronic acid. The hydrogel-forming polymer may also be a modified natural polymer, for example calcium pectinate, calcium alginate, modified egg albumin or modified soybean protein.

Naturally, delivery systems according to the invention in which the hydrogel-forming polymer belongs in said group (a), may also further optionally comprise at least one agent which inhibits enzymatic degradation of the drug in the intestine and/or at least one agent which is capable of enhancing the absorption of the drug across the intestinal mucosa.

In the drug delivery system of the invention, said matrix may comprise said hydrogel-forming polymer and at least one additional polymer. Examples of such additional polymers are hydrophobic acrylic acid derivatives such as Eudragit$^R$ RL, or suitable hydrogel-forming polymers such as hydroxypropylmethyl cellulose, methylcellulose, carboxymethyl cellulose or hydroxypropyl cellulose, or combinations thereof, natural polymers, such as guar gum, acacia gum, agar, tragacanth, alginic acid, dextran, arabinogalactan, pectin, egg albumin, soybean protein or hyaluronic acid, modified natural polymers, such as calcium pectinate, calcium alginate, modified egg albumin or modified soybean protein.

When emloying an absorption enhancer, this may be a medium-chained fatty acid, such as octanoic acid and decanoic acid, a fatty acid derivative such as palmitoyl-DL-carnitine or N-myristoyl-L-propyl-L-prolyl-glycinate, a non-steroidal anti-inflammatory drug such as sodium salicylate, sodium 5-methoxy-salicylate, indomethacin, diclofenac, a nonionic surfactant, such as poly-oxyethylene ether, an anionic surfactant, such as sodium laurylsulfate, a cationic surfactant, such as a quaternary ammonium compound, a dihydroxy bile salt, such as sodium deoxycholate, a trihydroxy bile salt, such as sodium cholate, a medium-chain glyceride, such as glyceryl-1-monooctanoate, an enamine, such as DL-phenylalanine, ethyl-acetoacetate enamine, mixed micelles such as glyceryl moolianoate+sodium taurocholate or linoleic acid+HCO60, a calcium binding agent, such as EDTA, a phenothiazine, such as chlorpromazine, liposomes, azone, a saponin, such as concanavaline A, or a phosphate and phosphonate derivative, such as DL-α-glycerophosphate or 3-amino-1-hydroxypropylidene-1,1-diphosphonate. Other absorption enhancers are also possible, and are known to the man versed in the art.

When adding an enzyme inhibitor, the inhibitor is suited to the drug entrapped in the matrix. Thus, for matrices containing protein or peptide drugs, the inhibitor may be any suitable protease inhibitor, for example, soybean trypsin inhibitor, aprotinin, diisopropylfluorophosphate, a-aminoboronic acid, sodium glycocholate or α-1-antitrypsin. Other protease inhibitors, as known to the man of the art may be suitable.

For matrices containing a drug which is susceptible to degradation by Cytochrome P-450, such as chlopromazine and flurazepam, the inhibitor may be any suitable cytochrome P-450 inhibitor, for example n-octylamine or propafenone. Other cytochrome P-450 inhibitors, as known to the man of the art may be suitable.

For matrices containing a drug which is susceptible to degradation by glucuronyl transferase, such as lorazepam or morphine, the inhibitor may be any suitable glucuronyl transferase inhibitor, for example an OH donor such as bilirubin. Other typical gulcuronyl inhibitors are tricyclic depressants, such as amiyriptriptyline, nortriptyline, comipramine or fluoxetin, in sub-therapeutical concentrations of $10^{-6}$M [Wahlstrom, A., et al. Pharmacology & Toxicology 75: 23–27 (1994)]. Another specific inhibitor is the novel site-directed inhibitor DHPJAdU [Pattaglya, E. et al., Biochem. Biophys. Acta 1243:9–14 (1995)].

The drug may be a protein drug may be any protein or peptide drug, for example, calcitonin, cyclosporin, insulin, oxytocin, tyrosine, enkephalin, tyrotropin releasing hormone (TRH), follicle stimulating hormone (FSH), luteinizing hormone (LH), vasopressin and vasopressin analogs, catalase, superoxide dismutase, interleukin-II (IL2), interferon, colony stimulating factor (CSF), tumor necrosis factor (TNF) or melanocyte-stimulating hormone. Other peptide or protein drugs, as known to the man skilled in the art, may also be contained in the pharmaceutical delivery system of the invention. Mixtures of the drugs are also contemplated.

The delivery system of the invention is also suitable for the delivery of drug other than protein or peptide drugs, which are susceptible to degradation by enzymes present in the intestine or in the intestinal mucosa. Examples of such drugs are cyclosporin, chlopromazine, ethinylestradiol and flurazepam, which are degraded by cytochrome P-450, and lorazepam and morphine, which are susceptible to degradation by glucuronyl transferase.

Other drugs, as known to the man skilled in the art, may also be contained in the pharmaceutical delivery system of the invention.

In addition to the above constituents, the different embodiments of the pharmaceutical delivery system according to the invention may also contain pharmaceutically acceptable adjutants.

The drug delivery system according to the invention is preferably in oral dosage unit form. Specific embodiments of prepared formulations of the protein drug delivery system of the invention include, for example, plain matrix tablets, especially tablets prepared by compression, multi-layered tablets or multi-particulate formulations, such as pellets or matrix-drug nanoparticles, which may be free or packed in gelatin capsules or any other means allowing oral administration. Techniques for preparation of such formulations are well known in the art, for example, as described in Remington's Pharmaceutical Sciences, Mack Publishing Company, 16th edition, 1980. In all embodiments, more than one drug may be supplied to the patient in the same matrix.

The oral dosage forms according to the invention may optionally be coated with another polymer for the purpose of increasing the product's stability upon storage or a suitable enteric coating material to protect it from the acidic environment of the stomach, as known to the man skilled in the art.

The therapeutic benefits of orally administered drugs, such as orally administered protein drugs, may depend upon the effective amount of the drug which is absorbed in the intestines of the patient. The delivery system according to the invention greatly increases the amount of intact drug, not degraded by the various enzymes present in the intestinal tract, which is absorbed. In addition, with most of drugs, controlled release, and thus absorption over long periods of time, is advantageous. The delivery system of the invention provides for such controlled release of the drug.

The amount of the drug can vary as desired for efficacious delivery of the desired drug and in consideration of the patient's age, sex, physical condition, disease and other medical criteria. In addition, the amount of the drug delivered by the system of the invention will depend upon the relative efficacy of the drug. The amount of specific drug necessary for efficacious results in the delivery system and methods of the invention may be determined according to techniques known in the art. For example, recommended dosages such as known in the art (for example, see the Physician's Desk Reference, 1991 (E. R. Barnhart, publisher). The Merck Index, 10th Edition, Merck & Co., New Jersey and The Pharmacological Basis of Therapeutics, 8th Edition, A. G. Goodman et al., eds., Pergamon Press, New York), provide a basis upon which to estimate the amount of drug which has previously been required to provide an efficacious level of activity.

The drug delivery system of the invention further provides a method for orally administering a drug to a patient in need thereof. In addition to the administration of protein or peptide drugs, the invention further provides a method for orally administering non-proteinous drugs having low bioavailability upon oral administration due to their high molecular weight (above 1,000 Da), or due to their susceptibility to brush border metabolism, or mixture of such drugs, to a patient in need thereof.

The invention also relates to a method of preparing the pharmaceutical delivery system according to the invention.

According to one specific embodiment the method of preparation of the delivery system according to the invention comprises the steps of (a) dissolving or suspending separately said hydrogel-forming polymer/s in non-aqueous media such as methanol; (b) in case two polymers are used mixing the two polymer solutions/suspensions obtained in step (a); (c) drying the mixtures obtained in step (b) into films; (d) grinding the dry films obtained in step (c); (e) suspending the ground mixtures obtained in step (d) in aqueous solution containing the drug and optionally the enzyme inhibitor and the absorption enhancer(s); (f) lyophilizing the mixture obtained in step (e); and (g) compressing the dry lyophilized polymer—drug mixture obtained in step (f) into dosage unit forms.

The following examples further describe the materials and methods useful in carrying out the invention. The examples in no manner are intended to limit the invention, which is defined by the scope of the appended claims.

EXAMPLES

Preparation of PCP—E-RL Hydrogels

Different polycarbophil (PCP)—Eudragit$^R$-RL (E-RL), a copolymer based on acrylic and methacrylic acid esters with a low content of quaternary ammonium groups available from Roehm Pharma, blends were prepared in different experiments by dissolving different (increasing) amounts of E-RL in methanol. This was followed by the addition of a constant amount (0.5 g) of PCP under stirring. The formed suspensions were then stirred until a homogenous, low-viscous gels were formed. The gels were poured onto a flat surfaces (petri dish), that were dried first at room temperature and then at 50° C. for 24 hours until thin films containing blends of different PCP—E-RL ratios were formed. The products were characterized for physical properties. Some of the properties were analyzed in film form (swelling, modulus of elasticity, torsion force) and some after tabletting (erosion, which was measured gravimetrically in PBS pH=7.5,relative to the dry weight of the tablets). The dependency on the E-RL contents in the gel blends and the torsion force was assessed from the best fitted line by using non linear regression.

Figure 2:
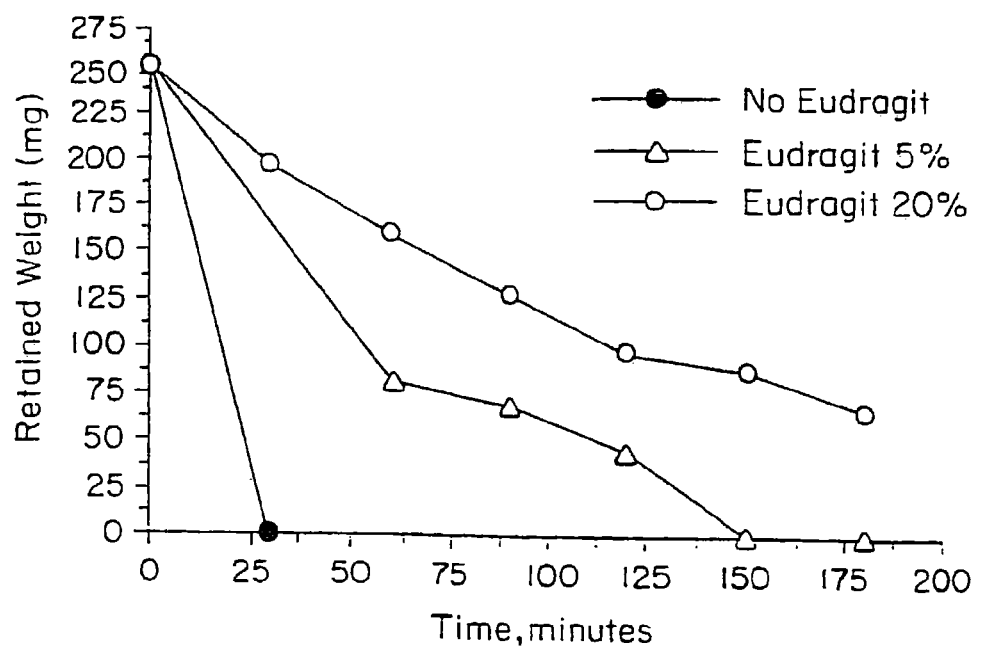
FIG. 2: Erosion rates of PCP tablets and two types of tablets made of blends of different ratios of PCP and Eudragit$^R$ RL (PCP containing 5% Eudragit$^R$ RL and PCP containing 10% Eudragit$^R$ RL) in a phosphate buffer, pH 6.8.
Figure 3:
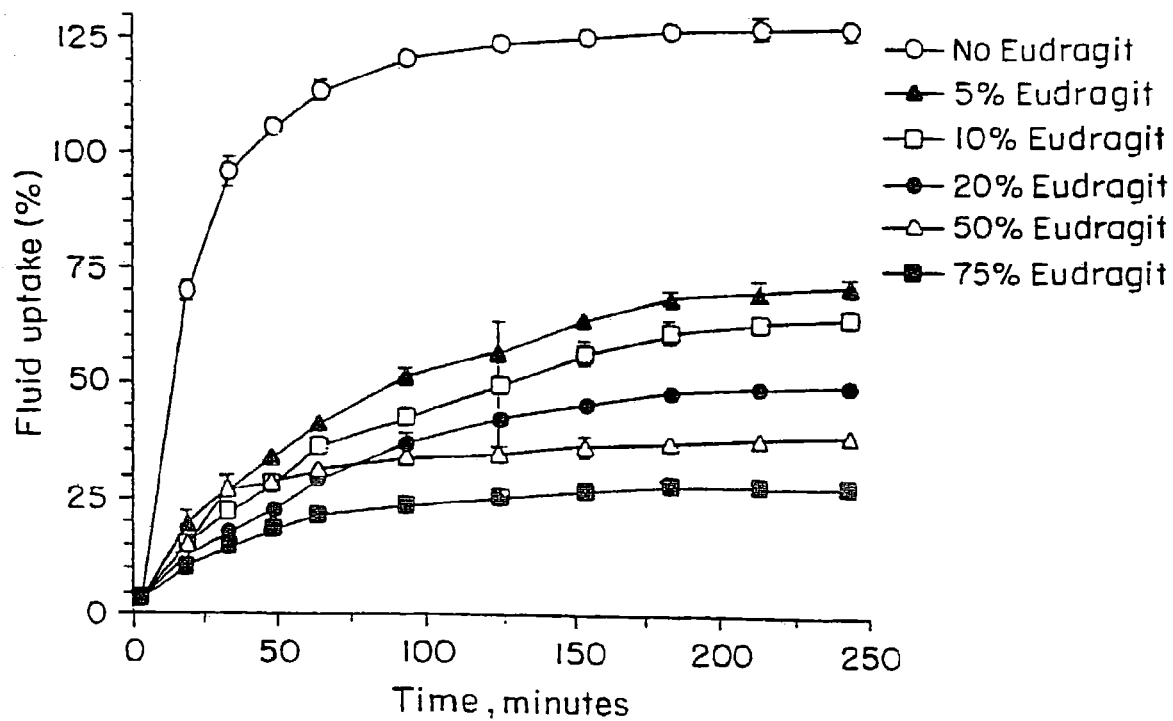
FIG. 3: The steady state swelling properties of PCP films and films made of different ratios of PCP-Eudragit$^R$ RL blends in phosphate buffer pH 7.5.
Figure 4:
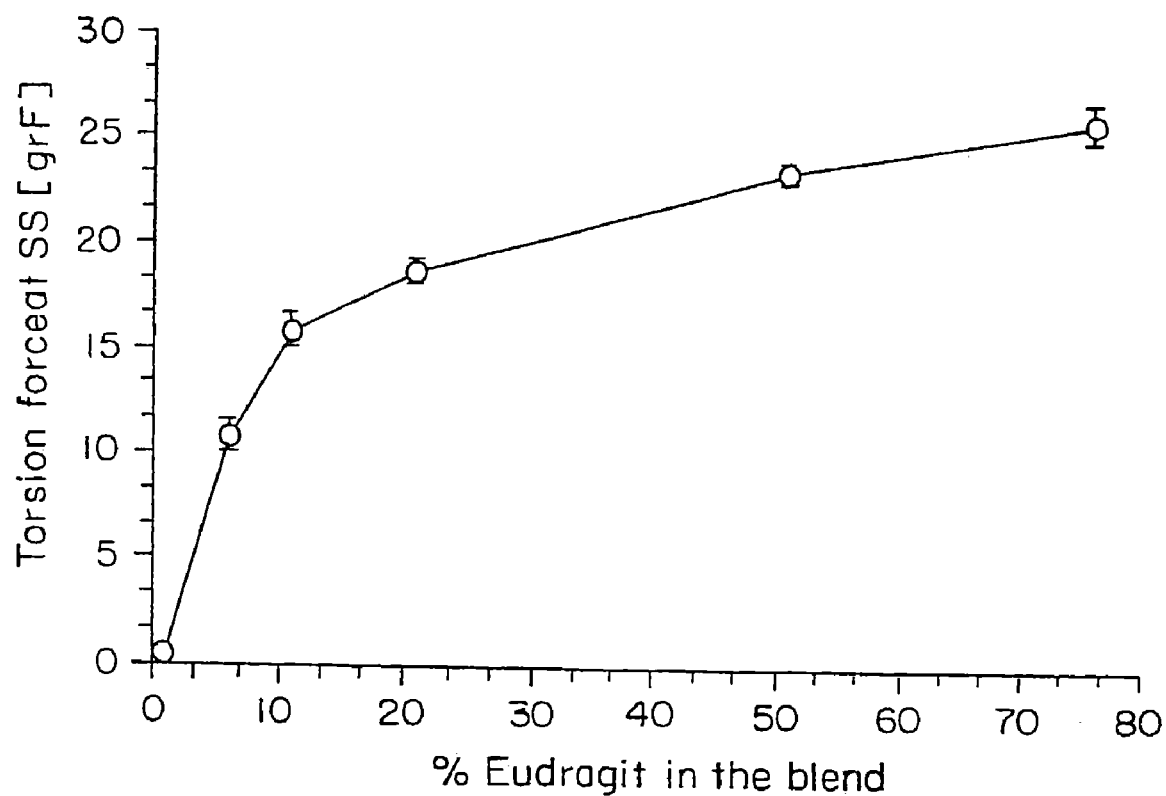
FIG. 4: The torsion force of different PCP-Eudragit$^R$ RL blends in swollen, steady state.

The ability of Eudragit$^R$ RL to modify the properties of the hydrogel is illustrated in FIGS. 2 to 4.

Thus, the ability of Eudragit$^R$ RL to control the erosion rates of the hydrogel is illustrated in FIG. 2 which demonstrates that a control over the erosion rate is accomplished by incorporating increasing amounts of Eudragit$^R$ RL into the PCP tablet.

The ability of Eudragit$^R$ RL to control the steady state swelling properties of the hydrogel is shown in FIG. 3 which demonstrates that Eudragit$^R$ RL significantly decreases the swelling properties of PCP and that the swelling is controllable by altering the Eudragit$^R$ RL amounts in the blends.

The ability of Eudragit$^R$ RL to control the torsion force of different PCP-Eudragit$^R$ RL blends in swollen, steady state is shown in FIG. 4 which demonstrates that Eudragit$^R$ RL increases, in a controllable manner, the torsion force of PCP in swollen blends of PCP and Eudragit$^R$ RL.

The ability of Eudragit$^R$ RL to control the modulus of elasticity of the hydrogel is summarized in Table 1.

TABLE 1

The modulus of elasticity (as characterized by Youngs modulus values) of different PCP-Eudragit$^R$ RL blends in swollen, steady state.

| | Concentration of Eudragit$^R$ RL in the blend (% w/W | | | | | |
|---|---|---|---|---|---|---|
| | 0 | 5 | 10 | 20 | 50 | 75 |
| Modulus of elasticity (g × cm$^2$) | 1,272 | 2,041 | 5,302 | 5,941 | 6,561 | 18,190 |

The Table demonstrates that Eudragit$^R$ RL increases, in a controllable manner, the Youngs modulus of PCP in swollen blends of PCP and Eudragit$^R$ RL.

The ability of PCP and PCP together with E-RL to protect the glucosidic substrate p-Nitrophenol-β-D-glucopyranoside (pNPG) against β-glucosidase was measured in aqueous suspensions of elevated concentrations of PCP (0.1% w/v and 0.2% w/v) and (in separate study) in PCP suspension (0.1% w/v) containing 5% w/v of E-RL.

Figure 5:
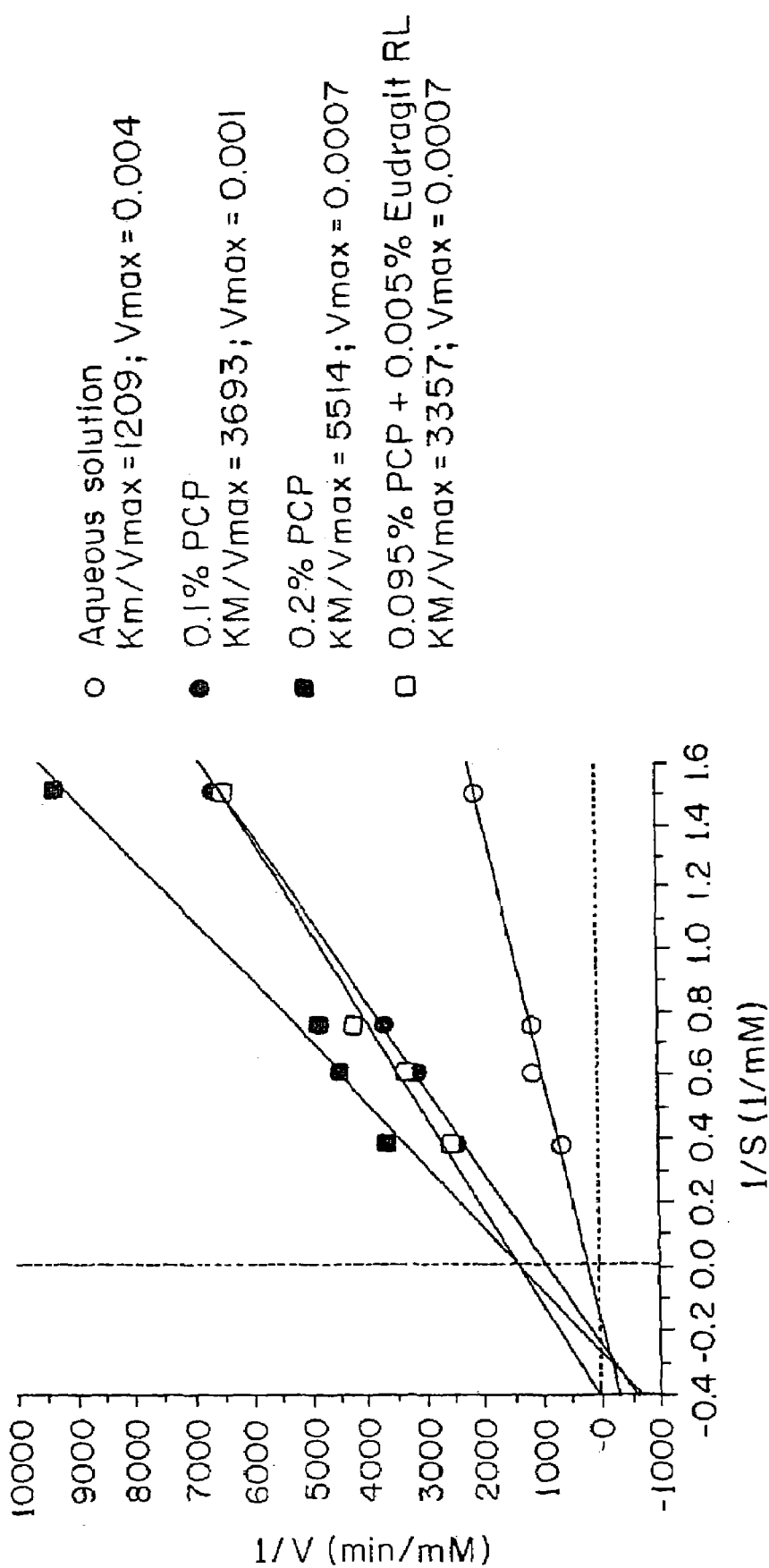
FIG. 5: Para-nitrophenol β-glucopyranoside (PNP-β-glucopyranoside) degradation kinetics resulted by incubation with β-glucosidase in aqueous solution and in the presence of two concentrations of PCP and a mixture of PCP and Eudragit$^R$ RL.

It was found that PCP was able to protect pNPG against enzymatic degradation in non-compatible manner and that E-RL did not interfere with this inhibition. As may be seen i9n FIG. 5, PCP is capable of inhibiting the activity of β-glucosidase in a concentration dependent manner and Eudragit$^R$ RL does not interfere with the inhibition activity of PCP. The kinetic profiles shown in FIG. 5 indicate that the inhibition of β-glucosidase by PCP is non-specific.

The Effect of PCP on the Enzymatic Degradation of Bradykinin

Fifty mg of bradykinin (Sigma) was incubated (37° C.) together with 0.5% w/w PCP suspension (pH 3.2). After 10 minutes 1 I.U. of α-chymotrypsin (Sigma) was added to the mixture and the incubation proceeded for additional 120 minutes.

Almost no bradykinin degradation could be detected. It is assumed that the α-chymotrypsin inhibition was caused by the acidic pH created by the PCP. It is assumed that if bradykinin will be mixed together with PCP to create a solid dosage form the resulted hydrogel which will be formed upon contact with water will provide a local protection (because of the formation of local low pH environment) to this protein drug against pancreatic enzymes [Lee V. H. L., CRC Crit. Rev. in Ther. Drug Carrier Systems, 5:69–139 (1989)].

Figure 6:
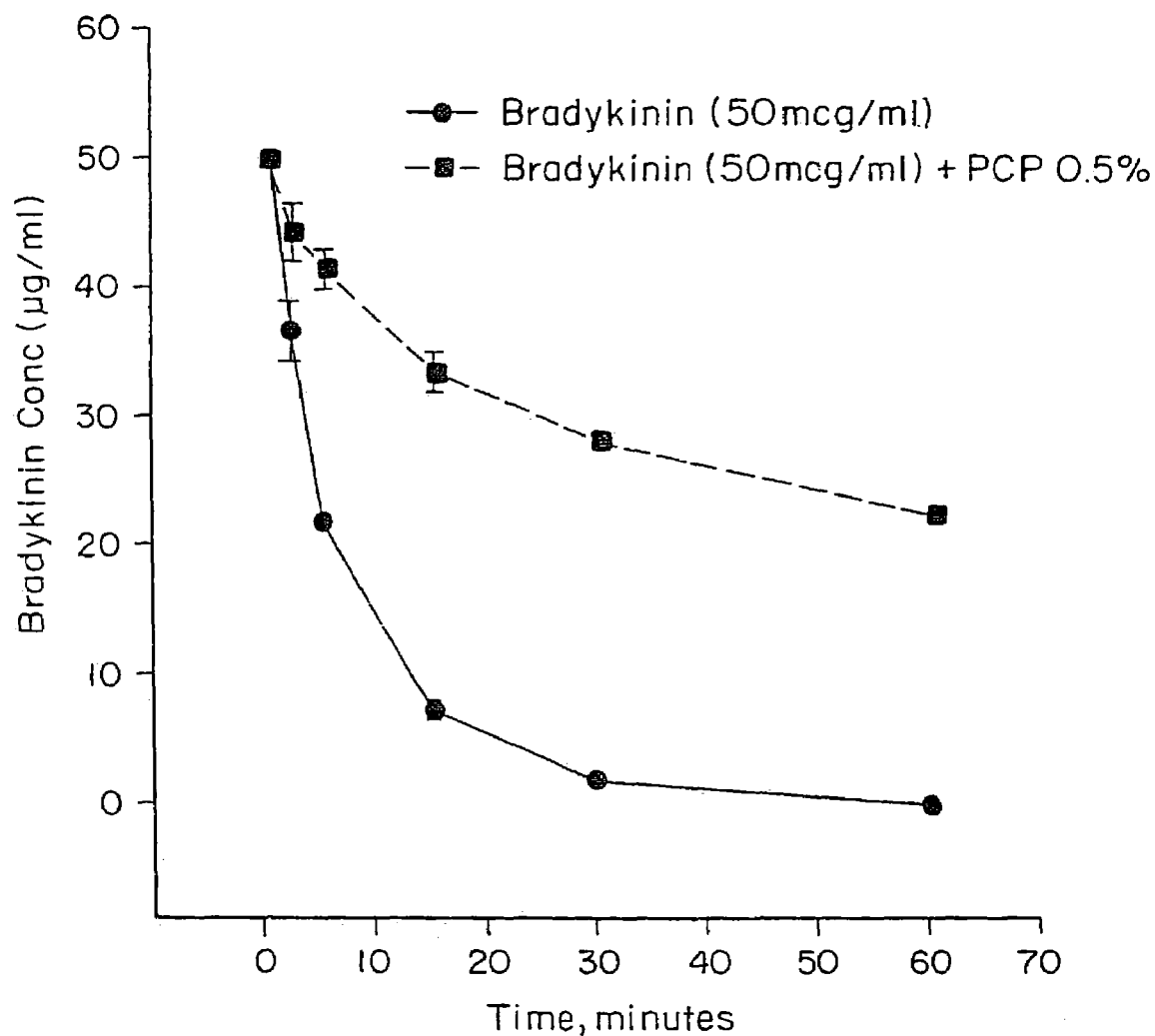
FIG. 6: The inhibition of bradykinin degradation by 0.5% w/v PCP suspension.

As may be seen in FIG. 6, PCP is able to inhibit the activity of α-chymotrypsin and hence to protect bradykinin from degradation.

Preparation of CaP-I Mixtures and Tablets

Insulin, sodium cholate (SC) and soybean trypsin inhibitor (SBTI) were mixed with 100 ml of the rinsed CaP gel [Rubinstein A. et al., Pharm. Res., 10:258, (1993)] in a dialysis bag prior to drying. The amount-ratio of the SC, SBTI and insulin to CaP was adjusted so that 500 mg of dry CaP contained 600 I.U. of insulin, 40 mg of SBTI and 100 mg of SC. The gel was lyophilized and the resulting dry CaP containing insulin, SC and SBTI was collected, comminuted to a fine powder, and sealed at 4° C. until further processing. Tablets were prepared from the dried gel powder. The plain matrix tablets were composed of 360 mg of CaP-insulin, 100 mg of SC and 40 mg of SBTI pressed at 5 KgP (Perkin Elmer manual press) to give a 500 mg tablet containing 600 I.U. of insulin each.

Preparation of Lactose-I Tablets

Lactose-I tablets were composed of 360 mg lactose-I, 100 mg sodium cholate (SC) and 40 mg soybean trypsin inhibitor (SBTI) pressed at 5 KgP to give a 500 mg tablet containing 600 I.U. of insulin.

In vivo Analysis of the Insulin-CaP Tablets in Dogs

Three mongrel dogs, weighing between 25 and 30 Kg were pancreatectomized, to achieve an immediate response to blood insulin alterations, and maintained on a daily intramuscularly introduced insulin. In three different experiments, CaP-I tablets were administered orally to the dogs. Each administration was performed after an overnight fast. No intra-muscular insulin was administered on the morning of the experiments. At pre-determined time intervals (every whole hour) blood samples were withdrawn from the cephalic vein of the dogs. This included a sampling one hour before each study (time 0).

Results

Figure 7A:
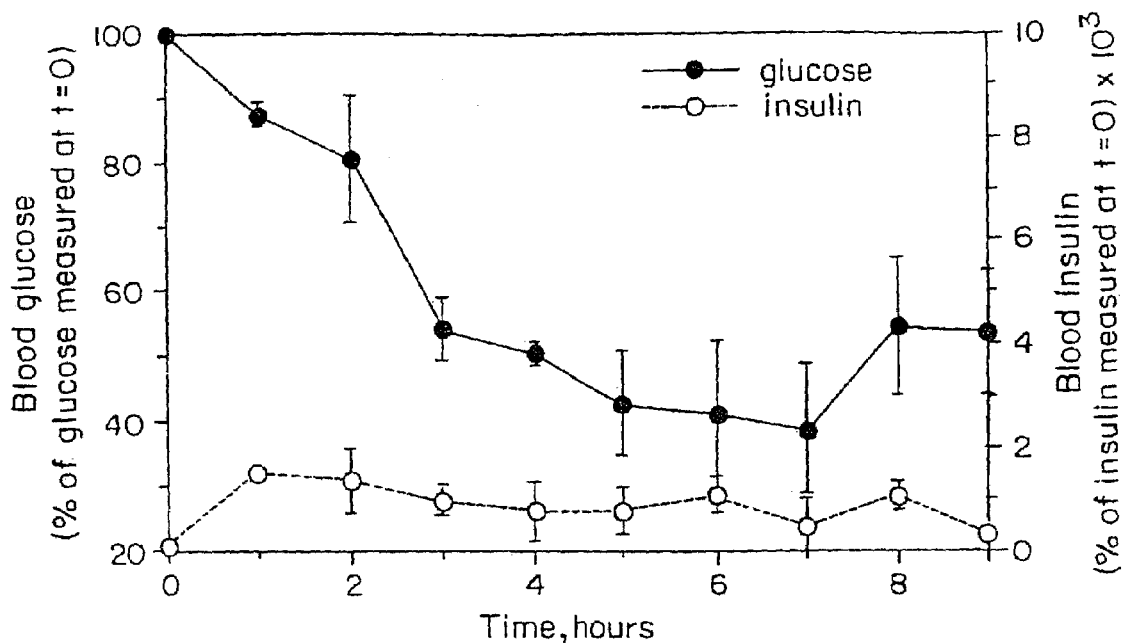
FIG. 7: A: Mean blood insulin levels and the resulting glucose levels after oral administration of calcium pectinate (CaP) tablets containing (a) 600 I.U. of insulin, (b) 40 mg of soy bean trypsin (SBTI) inhibitor and (c) 100 mg of sodium chocolate to three pancreatectomized dogs. Shown are the mean values±S.D.

The blood and glucose levels after oral administration of the tablets are shown in FIG. 7a. This Figure clearly demonstrates that the use of an erodible hydrogel matrix (in this case unprotected CaP) with a protein absorption enhancer (in this case sodium cholate) and, a protease degradation inhibitor (in this case (SBTI) results in sustained release of insulin, thus achieving constant levels of portal blood insulin. As a result, prolonged pharmacological response (over eight hours of reduced glucose levels) was achieved.

Figure 7B:
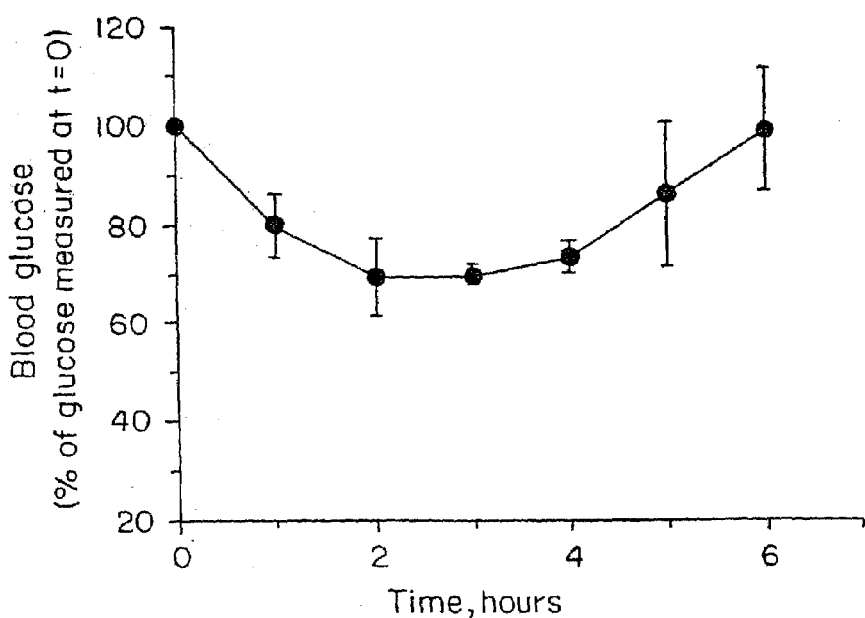

When tablets of the same composition, but with lactose instead of CaP were tested in the same dogs, typical non-sustained reduction in blood glucose levels was obtained (FIG. 7b). These results were expected since lactose dissolves in the GI fluids and does not form a hydrogel.

What is claimed is:

1. A synchronous drug delivery composition comprising an erodable, hydrogel-forming polymeric matrix which comprises:

a) a blend which comprises a hydrophulic polymeric cellulose derivative and a hydrophobic polymeric methacrylic acid derivative;

b) a drug;
c) an agent which enhances intestinal drug absorption; and
d) an enzyme inhibitor which inhibits intestinal drug degradation,
wherein erosion of said erodable matrix, permits synchronous release of said drug, said agent which enhances intestinal drug absorption and said agent which inhibits intestinal drug degradation.

2. A pharmaceutical composition comprising the synchronous drug delivery composition of claim 1 and a carrier or diluent.

3. A drug delivery composition according to claim 1, wherein the composition is in the form of a plain matrix tablet.

4. A drug delivery composition according to claim 1, wherein the composition is coated with an enterocoating.

5. A method of synchronically releasing a drug, an agent which inhibits intestinal drug degradation and an agent which enhances intestinal drug absorption, comprising the step of administering the composition of claim 1.

6. A method of increasing the bioavailability of a drug, comprising the step of administering the drug delivery composition according to claim 1.

7. A drug delivery composition according to claim 1, wherein said cellulose derivative is hydroxypropylmethyl cellulose, methylcellulose, carboxymethyl cellulose or hydroxypropyl cellulose.

8. A pharmaceutical composition comprising the synchronous drug delivery composition of claim 7 and a carrier or diluent.

9. A drug delivery composition according to claim 7, wherein the composition is in the form of a plain matrix tablet.

10. A drug delivery composition according to claim 7, wherein the composition is coated with an enterocoating.

11. A method of increasing the bioavailability of a drug, comprising the step of administering the drug delivery composition according to claim 7.

12. A drug delivery composition according to claim 1, wherein said methacrylic acid derivative is a dimethylaminoethylacrylate/ethylmethacrylate copolymer, wherein the molar ratio of the ammonium groups to the neutral (meth) acrylic acid esters is 1:20.

13. A pharmaceutical composition comprising the synchronous drug delivery composition of claim 12 and a carrier or diluent.

14. A drug delivery composition according to claim 12, wherein the composition is in the form of a plain matrix tablet.

15. A drug delivery composition according to claim 12, wherein the composition is coated with an enterocoating.

16. A method of increasing the bioavailability of a drug, comprising the step of administering the drug delivery composition according to claim 12.

* * * * *